(12) United States Patent
Jones et al.

(10) Patent No.: US 7,211,283 B2
(45) Date of Patent: May 1, 2007

(54) ENCASED FOOD PRODUCTS WITH CONTRASTING COMPONENTS

(75) Inventors: Adrienne Sarah Jones, York (GB); Mei Horng Ong, York (GB); Cristiana Fernanda Soldani, Milan (IT)

(73) Assignee: Nestec S.A., Vevey (CH)

( * ) Notice: Subject to any disclaimer, the term of this patent is extended or adjusted under 35 U.S.C. 154(b) by 201 days.

(21) Appl. No.: 10/408,816

(22) Filed: Apr. 8, 2003

(65) Prior Publication Data

US 2003/0219514 A1 Nov. 27, 2003

Related U.S. Application Data

(63) Continuation of application No. PCT/EP01/11369, filed on Oct. 1, 2001.

(30) Foreign Application Priority Data

Oct. 10, 2000 (GB) ................................ 0024810.4

(51) Int. Cl.
*A23G 3/34* (2006.01)
*A23G 3/48* (2006.01)
*A23G 3/54* (2006.01)

(52) U.S. Cl. ...................... 426/138; 426/573; 426/575; 426/660

(58) Field of Classification Search ................ 426/103, 426/661, 660, 573, 93, 575, 138
See application file for complete search history.

(56) References Cited

U.S. PATENT DOCUMENTS

| | | | |
|---|---|---|---|
| 1,711,750 A | 7/1929 | Shopper | |
| 4,101,650 A | 7/1978 | Umezawa | 424/44 |
| 4,209,536 A | 6/1980 | Dogliotti | 426/94 |
| 4,769,244 A | 9/1988 | Lavie | 426/96 |
| 5,302,396 A | 4/1994 | Phadke et al. | 424/465 |
| 5,437,873 A | 8/1995 | Phadke et al. | 424/465 |
| 5,607,716 A | 3/1997 | Doherty et al. | 426/660 |
| 5,985,341 A | 11/1999 | Ahlschwede | 426/93 |
| 6,299,915 B1 * | 10/2001 | Nussinovitch et al. | 426/89 |
| 2001/0036499 A1 | 11/2001 | Ong et al. | 426/573 |
| 2002/0001665 A1 | 1/2002 | Barrett et al. | 426/661 |

FOREIGN PATENT DOCUMENTS

| | | | |
|---|---|---|---|
| EP | 1023841 A1 * | 8/2000 | |
| EP | 1 104 652 A1 | 6/2001 | |
| JP | 58078542 A2 | 5/1983 | |
| JP | 3027233 A2 | 2/1991 | |
| JP | 7163301 A2 | 6/1995 | |
| WO | WO 93/22939 | 11/1993 | |

OTHER PUBLICATIONS

"Kids' Snack Gushes With Fruit Flavor," http://proquest.umi.com/pqdlink?did=88065611&sid=2&Fmt=3&clientId=19649&RQT=309&VName=PQD, Dec. 19, 1991.*
"Exemptions Under the Competitive Foods Regulation," http://www.cde.state.co.us/cdenutritran/download/pdf/ExemptionList05.pdf.*

* cited by examiner

*Primary Examiner*—Arthur L. Corbin
(74) *Attorney, Agent, or Firm*—Bell, Boyd & Lloyd LLP

(57) ABSTRACT

A food product that includes a casing of a gelatin-free, water-based, set hydrocolloid gel that forms an enclosure, and at least one solid, liquid, soft or particulate center enclosed by the casing. The casing is made of a carageenan, alginate, agarose, gellan gum, pectin or cellulose compound, and the food product can withstand changes in temperature. Also, a process for the production of such a food product, wherein a liquid hydrocolloid mass is partially set and a hard, liquid, soft or particulate center is injected therein with the final completing or the setting of the hydrocolloid mass providing the encapsulation of the center.

17 Claims, No Drawings

ENCASED FOOD PRODUCTS WITH CONTRASTING COMPONENTS

CROSS-REFERENCE TO RELATED APPLICATIONS

This application is a continuation of the US national phase of International Application PCT/EP01/11369 dated Oct. 1, 2001, the content of which is expressly incorporated herein by reference thereto.

FIELD OF THE INVENTION

The present invention relates to an encapsulated food product and more particularly to a food product comprising a gelatin-free water-based hydrocolloid casing surrounding a liquid, soil, hard or particulate centre.

BACKGROUND OF THE INVENTION

EP-A-64155 discloses a bite-sized edible confection or cocktail snack comprising a fat-based waterproof capsule surrounding a centre filling of high liquid content.

WO 97/35537 discloses a method for making capsules for pharmaceutical, cosmetic and dietary supplements with a very thin film/coating or layer of a material such as polyvinyl alcohol, alginate, hydroxypropyl methyl cellulose or polyethylene oxide made by a method based on a roller process. It is stated that polyvinyl alcohol film is available in thicknesses ranging between 20 and 1000 microns and that plasticised polyvinyl alcohol film having a thickness of 80 microns results in good quality capsules suitable for cosmetic use. There is no disclosure of the use of such capsules for use in foodstuffs.

Fat-based capsules have a tendency to crack in changing temperatures especially in tropical climates or where temperatures can reach 40° C. or above.

Neither of these patents disclose a food product having a casing, i.e. having a thickness of more than 0.1 mm, aqueous-based, and able to withstand changes in temperature without cracking nor a product exhibiting a contrasting appearance between the casing and the centre.

We have developed a food product comprising a gelatin-free water-based hydrocolloid casing enclosing a solid, liquid, soft or particulate centre which is capable of exhibiting a contrasting appearance between the casing and the centre. The casing may be substantially transparent or opaque and, in particular, when the casing is transparent, the contents of the centre may be clearly visible.

SUMMARY OF THE INVENTION

The present invention relates to a food product that includes a casing of a gelatin-free, water-based, set hydrocolloid gel, and at least one solid, liquid, soft or particulate center enclosed by the casing. The food product can withstand changes in temperature and exhibits a contrasting appearance or texture between the casing and the center.

DETAILED DESCRIPTION OF THE INVENTION

The casing may be substantially transparent or opaque.

The casing may have a thickness of between 0.1 mm and 10 mm, preferably from 1 to 7.5 mm, e.g. from 2 to 5 mm.

The hydrocolloid used in the casing may be carrageenan, alginate, agarose, gellan gum, pectin, or a cellulose derivative. The casing may be aerated to create opaqueness.

The food product of the invention is capable of exhibiting a contrasting appearance between the casing and the centre. The contrast may reside in the texture, colour, flavour or acidity of the centre compared with the casing.

Some liquid-filled gummy products are already on the market based on gelatin. However, food-grade gelatin is obtained from bovine or porcine raw materials and the use of gelatin is undesirable for the vegetarian population, as well as for certain ethnic groups who have concerns about the nature of meat used in certain food products and/or who observe certain dietary constraints concerning the consumption of meat and dairy products. We are not aware of any liquid-filled confections that are gelatin-free.

The amount of hydrocolloid in the casing may vary from 0.5 to 80% by weight depending on the thickness of the casing, e.g. for casings having a thickness of from 0.1–2 mm, the amount of hydrocolloid in the casing may be from 5–80% by weight the proportion of hydrocolloid preferably being higher the thinner the casing, and for casings having a thickness of from 2–10 mm, the amount of hydrocolloid in the casing may be from 0.5 to 5% by weight and preferably from 1 to 4% by weight based on the weight of the casing. The other main ingredients are water and sweetener. The water may be in an amount of from 3% to 50%, preferably from 7.5 to 40% and especially 10 to 20% by weight based on the weight of the casing. If desired, sugar, sugar syrup or sugar substitutes such as maltitol, lactitol, mannitol, xylitol, sorbitol, or artificial sweeteners may be present in the casing, e.g. the casing may, if desired, be sugar-free. Small amounts of acid, buffer or colourant may also be present in the casing The final solids content of the casing may be from 50 to 97%, preferably from 60 to 95% and especially from 75–85%.

The texture of the casing can vary from a plastic-like film to a water jelly to a fruit gum to a chew type texture (elastic to non-elastic).

The liquid or soft centre may contain water and sweetener, e.g. sugar, sugar syrup or sugar substitutes such as maltitol, lactitol, mannitol, xylitol, sorbitol, or artificial sweeteners, optionally together with oil/fat and other ingredients such as colour, flavour, acid or functional ingredients such as minerals, vitamins or herbs. The liquid centre can have a viscosity varying from that of water to the fluidity of glucose syrup at 25° C. (The viscosity of water @25° C. is 0.89 cP and that of glucose syrup 42DE @25° C. is 159000 cP).

The soft centre can vary from a paste, e.g. a chocolate, fat, or fruit paste, to a jelly to a chew texture. The solid centre may be, for instance, nut pieces, chocolate, fruit pieces, cheese, or hard-boiled pieces.

The particulate centre may be a powder, granular or an agglomerate having a particle size of from 25 to 2000 microns and may contain, for instance, sherbert, popping candy, sugar or sugar-substitutes such as maltitol, lactitol, mannitol, xylitol, sorbitol, or artificial sweeteners, and other functional ingredients such minerals, vitamins or herbal extracts.

The solids content of the liquid or soft centre may be from 50 to 90%, preferably from 60 to 85% and especially from 75–80%. The solids content of the hard centre may vary from about 50 to 99% e.g. for hard cheese (eg Cheddar) it may be from 60–65%, and for hard-boiled pieces it may be from 95–99%.

The weight ratio of the casing to the centre may range from 90:10 to 10:90, for example from 75:25 to 25:75.

The product may be used in hot, ambient, chilled and frozen applications, e.g. the product may be dropped in hot liquids at, for example, 80° to 100° C. to make hot drinks.

The product of the present invention may be a refreshing, clean eating sugar and/or sugar-free gelatin-free food product that is texturally interesting and visually attractive.

The product of the present invention may be a food product containing a single or multi-component centre with or without pieces. It may have a wide variety of shapes, e.g. spheres, hemispheres, cubes, cuboids, lentils, teardrops, pyramids, or cylinders.

The product of the present invention may conveniently have a diameter from 4 mm to 50 mm, preferably from 8 mm to 40 mm and more preferably from 10 mm to 25 mm.

The product of the present invention may deliver a centre of contrasting texture, flavour, colour, acidity to the coating and can offer significant differentiation to existing products. The product may also deliver active or functional ingredients such as minerals, vitamins or herbal extracts, etc.

The present invention also provides a process for the production of a food product comprising a gelatin-free water-based hydrocolloid-casing enclosing a hard, liquid, soft or particulate centre which comprises partially setting a liquid hydrocolloid mass to form the casing, e.g. in two halves or as a balloon and filled with a hard, liquid, soft or powder centre, and injecting with a hard, liquid, soft or powder centre and finally completing the setting of the hydrocolloid mass.

The injection of the liquid or soft centre may be carried out by means of a syringe or by one-shot depositing such as generally described in U.S. Pat. No. 1,711,750.

Most hydrocolloid systems set fairly quickly usually at about 40° to 90° C. when there is difference in temperature gradient, i.e. the gel sets quickly when in contact with something lower in temperature than itself. The bigger the temperature difference the quicker the setting. One exception is alginate which sets on contact with calcium ions.

Therefore, for water-based hydrocolloid casings excepting alginates enclosing a liquid or soft centre, the food product may be prepared by depositing a liquid hydrocolloid mass at a temperature above its setting temperature, e.g. 40°–90° C., in a mould which is at a lower temperature than the liquid hydrocolloid mass, and injecting with a liquid or soft centre at a temperature lower than the temperature of the hydrocoloid mass while the hydrocolloid mass is still soft until it sets. Preferably, the hydrocolloid mass is cooled to speed up the setting of the gel and to ensure the centre stays central.

The injected centre at a lower temperature than the liquid hydrocolloid mass is conveniently at a temperature from 5° C. to 50° C., preferably from 8° C. to 30° C., and especially from 10° C. to 15° C.

The injected centre at a lower temperature than the liquid hydrocolloid mass causes the hydrocolloid mass to set immediately on contact, thereby encasing the centre within the gel.

If desired, the liquid hydrocolloid may be deposited into a bubble pack lining the mould or into pots which form the packaging, for instance, by one-shot depositing.

For water-based hydrocolloid casings excepting alginates enclosing a hard or particulate centre, the food product may be prepared by lining a mould with a liquid hydrocolloid mass at a temperature above its setting temperature, e.g. from 40° C. to 100° C., the mould being at a lower temperature than the liquid hydrocolloid mass, to form a shell open at one end, inserting the hard or particulate centre into the shell, and backing off with a layer of hydrocolloid casing.

For a water-based alginate casing, the food product may be prepared by depositing a liquid alginate mass in an aqueous medium containing preferably calcium ions to form a semi-set pliable casing instantaneously, surrounding the liquid alginate mass, injecting with a liquid or soft centre and finally completing the setting of the alginate mass. The setting will occur with time but, if desired, cooling will help speed up the setting, e.g. in an aqueous medium around 10° C.–20° C. For achieving the desired shape, the liquid alginate mass is deposited into a mould submerged in the calcium bath, the mould having fine holes in the base which allows the aqueous medium to circulate around the mass thereby causing it to set.

The aqueous medium containing calcium ions may contain from 0.1% to 5% preferably from 0.5 to 2%, depending on the solids content of the hydrocolloid mass of an edible calcium salt, e.g. calcium acetate, calcium citrate, calcium tartrate, calcium lactate, calcium propionate or calcium carbonate but preferably calcium chloride.

The thickness of the casing depends on the length of time the alginate gel is in contact with the calcium ions.

In a further embodiment, the present invention provides a food product comprising two or more gelatin-free water-based hydrocolloid casings connected together each casing enclosing a solid, liquid, soft or particulate centre.

The casings may be substantially transparent or opaque.

The centres within the casings may be the same or different. When the centres are different, they may comprise materials which are reactive with one another, the reaction taking place when the casings are destroyed on consumption. For example, the reaction may include the release of a gas such as carbon dioxide, e.g. where one centre comprises an alkali such as sodium bicarbonate and another centre comprises an acid, e.g. a fruit acid such as citric acid. Advantageously, in addition to the reactive materials, at least one of the centres may comprise other materials such as flavours, e.g. champagne concentrate. The two centres may be made, for instance, by injecting with two needles. The food product comprising two or more gelatin-free water-based hydrocolloid casings connected together may be made by sticking two or more casings together when they are wet.

The product of the invention is a sugar/sugar-free/functional food product that is gelatin-free, visually interesting and extremely striking, combining a textural difference and an immediate flavour impact, and which delivers clear differentiation from existing products on the market.

Compared with the fat-based capsule described in EP-A-64155, the product of the invention has a different texture ranging from plastic to elastic to non-elastic and the absence of fat (only if the centre doesn't contain fat or oil) makes the product cleaner and more refreshing to eat

EXAMPLES

The following Examples further illustrate the present invention. Parts and percentages are given by weight.

Example 1

A Carrageenan Gum mass having a total solids content of 77% and a pH of 3.8 to 4.0 for the gel casing is prepared by mixing the ingredients of the following recipe:

| Gum Recipe | % |
| --- | --- |
| Sugar syrup | 57 |
| Sugar | 20 |
| Water | 19 |
| Carrageenan | 2.4 |
| Acid | 1.6 |
| Buffer | 0.8 |

The gum mass at a temperature of 90° C. is deposited into a mould at 25° C. and is injected by a syringe with a liquid centre at 15° C. while still soft. The liquid centre is prepared by mixing the ingredients of the following formulation:

| Liquid Centre | % |
| --- | --- |
| Sugar syrup | 99.5 |
| Colour | 0.004 |
| Flavour | 0.4 |

This results in a visually extremely striking product. One processing option for these products might be to mould directly into bubble packs or deposit into pots or moulds by one-shot depositing.

Example 2

An alginate gum mass having a total solids content of 75% and a pH of 3.8–4.0 for the gel casing is prepared by mixing the ingredients of the following recipe:

|  | % |
| --- | --- |
| Sugar | 48 |
| Sugar syrup | 20 |
| Alginate | 1.5 |
| Water | 30 |
| Glyceryl monostearate | 0.2 |
| Trisodium orthophosphate | 0.3 |
| Flavour | 0.04 |

The Alginate mass at 85° C. is deposited into a calcium bath containing 99.5% water and 0.5% calcium lactate at 20° C. and allowed to set. A semi-set casing forms after about 5 minutes leaving the centre of the product liquid.

The liquid centre at a temperature of 15° C. is injected with a syringe through the semi-set casing. The casing sets fully over a period of time which may vary from 5 minutes to 120 minutes. This results in a soft product with a liquid centre.

The liquid centre is prepared by mixing the ingredients of the following formulation:

| Liquid Centre | % |
| --- | --- |
| Sugar syrup | 99.5 |
| Colour | 0.004 |
| Flavour | 0.4 |

What is claimed is:

1. A food product comprising a fat-free casing including an at least substantially transparent, gelatin-free, water-based, set hydrocolloid gel that forms an enclosure, and at least one solid, liquid, soft or particulate center enclosed by the casing, wherein the product exhibits a contrasting appearance and texture between the casing and the center, and wherein the food product is selected from the group consisting of gums, jellies, hydrocolloid compositions and combinations thereof.

2. The food product according to claim 1 wherein the hydrocolloid gel is selected from the group consisting of carrageenan, alginate, agarose, gellan gum, pectin or a cellulose compound.

3. The food product according to claim 1 wherein the hydrocolloid gel is present in the casing in an amount of from 0.5 to 80% by weight based on the weight of the casing.

4. The food product according to claim 1 wherein the casing includes water in an amount of from 3 to 50% by weight based on the weight of the casing.

5. The food product according to claim 1 wherein the casing further comprises a sweetener, and wherein the casing is transparent so that the center is visible therethrough.

6. The food product according to claim 5 wherein the sweetener is a sugar or sugar syrup, a sugar substitute or an artificial sweetener.

7. The food product according to claim 1 wherein the center is a liquid or soft center containing a sweetener and water together with one or more of a color, flavor, acid and functional ingredients.

8. The food product according to claim 7 wherein the sweetener is a sugar or sugar syrup, a sugar substitute or an artificial sweetener, and the functional ingredients are minerals, vitamins or herbal extracts.

9. The food product according to claim 1 wherein the center is a liquid center having a viscosity of 0.89 cp to 159000 cp.

10. The food product according to claim 1 wherein the center is a soft center having the texture of a jelly, a fruit gum, a chew or a paste.

11. The food product according to claim 1 wherein the center is a hard center that contains nut pieces, fruit pieces, cheese, chocolate or hard-boiled candy.

12. The food product according to claim 1 wherein the center is a particulate center that contains sherbert, popping candy, a sugar or sugar syrup, a sugar substitute, or an artificial sweetener, and which may also contain one or more of a color, flavor, acid or functional ingredient.

13. The food product according to claim 1 wherein the casing and center are present in a weight ratio of 90:10 to 10:90.

14. The food product according to claim 1 wherein the casing has a diameter of 4 mm to 50 mm.

15. A food product comprising two or more fat-free casings connected together, each casing including an at least; substantially transparent, gelatin-free, water-based, set hydrocolloid gel, each casing enclosing a solid, liquid, soft or particulate center, wherein the food product exhibits a contrasting appearance and texture between each casing and its center and wherein the food product is selected from the group consisting of gums, jellies, hydrocolloid compositions and combinations thereof.

16. The food product according to claim 15, wherein the centers are different.

17. The food product according to claim 15, wherein the casings are transparent so that the centers are visible therein.

* * * * *